United States Patent [19]
Griat et al.

[11] Patent Number: 5,489,429
[45] Date of Patent: Feb. 6, 1996

[54] WATER-IN-OIL EMULSION CONTAINING POLYOLS AND ITS USE IN COSMETOLOGY

[75] Inventors: Jacqueline Griat, Ablon; Jacqueline Lambert, Paris; Philippe Touzan, Ramonville Saint Agne, all of France

[73] Assignee: L'Oreal, Paris, France

[21] Appl. No.: 314,292

[22] Filed: Sep. 30, 1994

[30] Foreign Application Priority Data

Oct. 29, 1993 [FR] France .................................. 93 12918

[51] Int. Cl.⁶ ..................................................... A61K 7/48
[52] U.S. Cl. ......................... 424/401; 514/847; 514/943; 514/785
[58] Field of Search ..................................... 514/847, 943; 424/401

[56] References Cited

U.S. PATENT DOCUMENTS 4,089,879  5/1978  Naskar .................................. 260/410.7

*Primary Examiner*—C. Warren Ivy
*Assistant Examiner*—Evelyn Huang
*Attorney, Agent, or Firm*—Oblon, Spivak, McClelland, Maier & Neustadt

[57] ABSTRACT

The invention relates to an emulsion containing an aqueous phase dispersed in an oily phase using a mixed ester of isostearic acid and succinic acid with glycerol, and at least 10% by weight of polyol relative to the total weight of the emulsion.

This emulsion is intended in particular for the cosmetic and/or dermatological treatment of hands.

15 Claims, No Drawings

WATER-IN-OIL EMULSION CONTAINING POLYOLS AND ITS USE IN COSMETOLOGY

The present invention relates to a water-in-oil (W/O) emulsion containing polyols. This emulsion is present in the form of a cream which may serve as a base for obtaining a white or coloured cream, intended in particular for the cosmetic treatment (via the topical route) of the face, the body, the legs and more especially the hands, for the purpose of protecting them.

By incorporation of an appropriate active agent, this cream may in addition serve for the dermatological treatment of the same areas of the body.

In the cosmetics field, it is common to use creams consisting of a water-in-oil emulsion containing polyols as moisturizing agent or humectant.

Thus, document JP-A-58/105906 describes a cream of the water-in-oil type containing from 1.5% to 60% by weight (relative to the total weight of the cream) of polyol and a hydrophobic surfactant of the polyglycerol ester type.

Moreover, document JP-A-43/60821 teaches about a cream for the topical treatment of dry skin types, of the water-in-oil type containing 15% to 45% by weight (relative to the total weight of the cream) of glycerol and an emulsifying agent with an HLB value of 8 to 11. The HLB (hydrophilic/lipophilic balance) represents the equilibrium between the size and strength of the hydrophilic group and the size and strength of the lipophilic group of the emulsifying agent.

On account of their high polyol content, these creams have the disadvantage of imparting to skin, after application, a highly sticky nature comparable to that of glue. This sticky nature may be prohibitive as regards their use for the hands, by momentarily depriving the user of these precious tools.

It is moreover known from document WO-A-93/00880 to use polyol in high content (15% to 30% by weight) in water-in-oil creams which, although containing no preserving agent, have antimicrobial properties. These creams have the same disadvantages as those of the creams cited above.

In order not to exhibit this sticky nature, the creams currently used specifically for the treatment of hands are water-in-oil emulsions containing a low content of polyol (generally of the order of 5%). The aim of these creams is to soften, to render supple and to protect the skin of the hands, as wall as to reduce redness and/or chapping. Examples of hand creams are described in particular in document JP-A-43/70152.

Unfortunately, these creams have a very relative effectiveness, not allowing the treatment of cracks and leaving the hands dry.

In terms of effectiveness, the cream of reference for the treatment of hands which is currently on the market is the NEUTROGENA® "Norwegian formula", "Concentrated" cream containing glycerol. This film-forming cream, which is particularly effective against redness and chapping, nevertheless has the disadvantages of a texture and an appearance which are rather unattractive, and unsatisfactory skin penetration and supplying properties. In addition, the hands, even after treatment, are still too dry.

The need thus remains for a handcare cream not having a sticky nature, having a good penetration and a noteworthy anti-drying effect, and which makes it possible to reduce redness, chapping or even cracks.

Precisely, the subject of the invention is a water-in-oil emulsion which is appropriate for the cosmetic and/or dermatological treatment of the hands. This emulsion may also serve for the treatment of the face, the body and the legs.

More precisely, the invention relates to an emulsion containing an aqueous phase dispersed in an oily phase using an emulsifying agent, characterized in that this emulsifying agent is formed essentially of a mixed ester of isostearic acid and succinic acid with glycerol and in that the emulsion additionally contains at least 10% by weight of polyol relative to the total weight of the emulsion.

This emulsion of high polyol content may advantageously be used for the treatment of the hands. surprisingly, it imparts almost no sticky effect to the hands. Moreover, on account of its high polyol content, it penetrates efficiently into the skin and in particular ensures a good moisturization and a high degrees of supplying of the latter, as well as a high penetration into the skin leading to a reduction in redness and chapping.

Although it is certainly known from the document FR-A-2,686,510 to use a mixed ester of isostearic acid and succinic acid with glycerol as emulsifying agent in a water-in-oil emulsion, this emulsifying agent is necessarily associated with a silicone-containing emulsifying agent. Indeed, the problem which the subject of this document sought to resolve was the incorporation of large amounts of silicones.

According to the invention, the polyol content may represent up to 40% by weight relative to the total weight of the emulsion, and may preferably be chosen from 12% to 30% and, for example, from 12% to 20%.

Glycerol, mannitol, sorbitol, glucose and sugar derivatives, as well as diglycerol, may be used as polyol in the invention. These polyols may be used alone or as a mixture.

Water-in-oil emulsions which may be used in cosmetology, containing a mixed ester of isostearic acid and succinic acid with glycerol as emulsifying agent and a polyol (glycerol) in a low content of 3% by weight relative to the total weight of the emulsion, are known from document U.S. Pat. No. 4,089,879.

If these emulsions were used on the hands, this low polyol content would not provide the desired suppleness or moisturizing properties, the desired anti-drying effect, or provide a sufficient penetration of this emulsion into the skin.

In addition, this document does not suggest increasing the amount of glycerol in order to obtain these properties.

Finally, a stable water-in-oil emulsion is very difficult to produce and is a judicious choice of the various constituents in well-defined proportions. Also, the emulsion may be broken simply by changing the product or the concentration.

The esterification of glycerol in the emulsifying agent according to the invention may be partial or total. It may be performed as described in document U.S. Pat. No. 4,089,879. In particular, the mixed ester used is that sold by the company Hüls, under the name of Imwitor 780K and corresponding to isostearyl diglyceryl succinate (according to the CTFA nomenclature).

This emulsifying agent has the advantage of being stable to oxidation, of not turning stale and of being non-toxic and perfectly compatible with the skin.

The association of this emulsifying agent with a high polyol content imparts most of its properties to the emulsion.

The emulsifying agent is preferably used at a content of 0.5% to 8% by weight relative to the total weight of the emulsion, and better at a content of 2% to 5% by weight.

With a view to improving the cosmetic properties of the emulsion, it is advantageous to use volatile silicones, alone or as a mixture, in the oily phase, for example such as linear silicones containing from 1 to 4

groups such as hexamethyldisiloxane and octamethyltrisiloxane; cyclic silicones such as octamethylcyclotetrasiloxane and decamethylcyclopentasiloxane (known as cyclodimethicones according to the CTFA nomenclature).

It is, however, possible to use other oils, such as vegetable (jojoba or apricot) oils, inorganic oils (liquid paraffin), or synthetic oils (purcellin oil), or alternatively fluorinated oils (perfluoropolyether).

The oily phase represents from 10% to 45% by weight relative to the total weight of the emulsion and preferably from 20% to 30%.

In addition, the silicones may represent all or part of the oily phase. The other oils generally represent only 1% to 10% by weight relative to the total weight of the oily phase.

In order to ensure a good conservation of the emulsion with time, it is possible to incorporate therein a preserving system containing one or more compounds, for example chosen from alkyl parahydroxybenzoates (CTFA name), formaldehyde-liberating agents (imidazolidinylurea), chlorphenesin, and the like.

The preserving system may represent from 0.1% to 1% by weight relative to the total weight of the emulsion.

It is additionally possible to add to the emulsion other adjuvants such as perfumes, lipophilic gelling agents (Bentone, was or gum) or hydrophilic gelling agents (chitosan), dyestuffs, active agents, and all the adjuvants conventionally used in the cosmetic and dermatological fields.

Active agents which may be used are hydrophilic active agents such as proteins or protein hydrolysate (restructuring agent), allantoin (anti-inflammatory agent), flower waters (softening agent), chitosan (humectant), amino acids and panthenol (moisturizing agent and calmant), α-hydroxy acids and urea, as well as lipophilic active agents such as vitamins A and E and the esters thereof (regenerating and protecting agent), α-bisabolol (anti-inflammatory agent), ceramides (for cell cohesion) and essential fatty acids (nourishing agent).

It is also possible to use UV filters having a lipophilic or hydrophilic property.

The dyestuffs may be either pigments (from oxide or titanium oxide) or organic dyes (Ponceau disodium salt).

As indicated above, the emulsion of the invention may advantageously be used for the dermatological and cosmetic treatment of the human face and body, and more especially of the hands.

For the face, the emulsion of the invention may serve as a base in order to form, for example, a care cream, a sun cream or alternatively a moisturizing mask.

Also, another subject of the invention is a cosmetic composition formed of an emulsion as defined above, as well as the use of this emulsion for the cosmetic treatment of the hands.

Another subject of the invention is the use of this emulsion for the preparation of a cream intended for the dermatological treatment of the hands.

Other characteristics and advantages of the invention will emerge more clearly from the description which will follow, given as a guide and without any limitation being implied.

The emulsion of the invention is obtained by firstly introducing into the oily phase the fatty acid mixed ester, optionally containing the lipophilic compounds (active agents, perfumes, dyes and gelling agents), and then by homogenizing the whole mixture at 40° C.; at the same time, the polyols are dissolved at room temperature is optionally-demineralized water, followed by the preserving agents and the hydrophlic active agents, Next, the aqueous phase is introduced into the oil phase, still at 40° C., with vigorous stirring which is maintained for approximately 10 minutes. Finally, the whole mixture is cooled to 20° C.

A stable, smooth and shiny cream of attractive, clear appearance is thus obtained.

In the examples below, all the creams obtained are light, clear, pleasant-smelling and non-sticky after application. In addition, the amounts are given in % by weight.

EXAMPLE 1

Reparatory and Protective Hand Care Cream

| Lipophilic phase | |
|---|---|
| Imwitor 780 K (isostearyl diglyceryl succinate) | 3 |
| Octyldodecanol | 4 |
| Octylmethoxycinnamate (Parsol McX sold by Givaudan) (filter) | 2 |
| Quaternium-18 Hectorite (Bentone) (gelling agent) | 2 |
| Cyclomethicone (volatile silicone) | 20 |
| Perfume | 0.2 |
| Hydrophilic phase | |
| Glycerol | 10 |
| Sorbitol | 5 |
| Preserving agents | 0.5 |
| Vegetable protein (restructuring agent) | 0.2 |
| Demineralized water qs | 100 |

EXAMPLE 2

The emulsion of this example differs from that of Example 1 by the introduction of iron oxide to a concentration of 0.0024% by weight in order to give the cream a slightly pink colour.

EXAMPLE 3

Nutritive and Protective Face Care Cream

| Lipophilic phase | |
|---|---|
| Avocado oil | 7 |
| Imwitor 790 K | 5 |
| Cyclomethicone | 13 |
| Octyldodecanol | 3 |
| Synthetic ceramide | 0.05 |
| Mixture of cyclomethicone and dimethicone (silicone gum) | 6 |
| Parsol MCX | 2 |
| Perfume | 0.3 |
| Hydrophilic phase | |
| Marine collagen (softening agent) | 0.5 |
| Proline (regenerating agent) | 1 |
| Mannitol | 5 |
| Glycerol | 12 |
| Chitosan PCA (Kytamer PC, supplied by Amerchol) (gelling agent) | 0.2 |
| Preserving agents | 0.5 |
| Water qs | 100 |

EXAMPLE 4

Protective and Anti-drying Sun Cream for the Face and Body

| Lipophilic phase | |
| --- | --- |
| Cyclomethicone | 20 |
| Parsol MCX | 5 |
| Titanium dioxide (filtering filler) | 3 |
| Karite butter (oil) | 5 |
| Imwitor 780 K | 4 |
| Bentone (gelling agent) | 3 |
| Perfume | 0.3 |
| Preserving agent | 0.2 |
| Hydrophilic phase | |
| Dyes | 0.1 |
| Glycerol | 15 |
| Preserving agents | 0.4 |
| Water qs | 100 |

EXAMPLE 5

Moisturizing and Nutritive Body Cream

| Lipophilic phase | |
| --- | --- |
| Imwitor 780 K | 4 |
| Octyldodecanol | 4 |
| Apricot oil | 8 |
| Cyclomethicone | 12 |
| Synthetic ceramide | 0.1 |
| Silicone gum | 6 |
| Hydrophilic phase | |
| Preserving agents | 1 |
| Glycerol | 12 |
| Mannitol | 8 |
| Crosslinked starch (Dry-Flow + from National Starch) (matting − softening agent) | 0.3 |
| Chitosan PCA (gelling agent) | 0.2 |
| Urea (moisturizing agent) | 1 |
| Demineralized water qs | 100 |

EXAMPLE 6

Reparatory and Protective Hand Care Cream

| Lipophilic phase | |
| --- | --- |
| Imwitor 780 K (isostearyl diglyceryl succinate) | 3 |
| Octyldodecanol | 4 |
| Octylmethoxycinnamate (Parsol McX sold by Givaudan) (filter) | 2 |
| Quaternium-18 Hectorite (Bentone) (gelling agent) | 2 |
| Cyclomethicone (volatile silicone) | 20 |
| Perfume | 0.2 |
| Hydrophilic phase | |
| Glycerol | 35 |
| Mannitol | 5 |
| Preserving agents | 0.5 |
| Demineralized water qs | 100 |

The cream obtained has virtually no sticky effect, despite the 40% polyol content.

The hand cream of Example 2 and the NEUTROGENA hand cream were tested in parallel for two weeks on two similar panels of 18 persons and 11 persons respectively.

This consisted of women with very damaged hands on account of their working conditions, on the one hand, and on account of the harsh climate, on the other hand.

Approximately ⅓ of them displayed either redness or chapping, and sometimes both.

The palms of the hands were often very impaired.

The cream of the invention obtained better cosmetic scores than the NEUTROGENA cream as regards:

The penetration: 94% favorable opinions instead of 59%

The texture: 89% favourable opinions instead of 65%

The cream of the invention obtained 100% favourable opinions as regards its spreading and only 2 persons mentioned the presence of a greasy film on the hands. The presence of a waxy film is likened to a protective effect, and therefore does not have a negative connotation.

As regards the effectiveness, these two creams were judged to be equivalent for protection against the cold and against water, and for the softness of the hands.

On the other hand, the cream of the invention was judged to be superior as regards the suppleness of the skin (72% "satisfactory" against 41%) and the anti-drying effect (83% "satisfactory" against 47%).

For persons having chapping and cracks, the cream of the invention has been recognized as being more effective than the NEUTROGENA cream.

In conclusion, the cream of the invention was judged to be superior in allying cosmetic appeal than the NEUTROGENA cream, with a treating action and an effectiveness of higher performance. However, the NEUTROGENA hand cream was hitherto considered to be the most effective for hand care.

Moreover, the cream of Example 2 was subjected to a test on the public, on thirty women whose hands were dry or very dry and who, for the majority, had problems of the chapping, redness or scaling type, or simply dehydration streaks.

After using for 3 weeks, the majority of these people were able to observe a marked improvement in the state of their hands. The skin is considerably less dry, softer and more supple for 65% of the sample.

The protective and moisturizing effects are noticed to a lesser extent, but are nevertheless above average and arrive at a respective total of 51% to 56% ("very considerable" or "considerable").

In addition, ¾ of the people having chapping or cracks saw an attenuation of their problem, the majority of whom evaluate it as being very considerable or considerable.

The cosmetic properties of this cream were very much appreciated: easy to apply, light, well-balanced grease content.

The comfort provided is good and long-lasting, and the odour is pleasant.

Approximately ¾ of the users were thus satisfied with this cream and would buy it to replace their usual product.

The almost exclusive reason for satisfaction given is the effectiveness of this cream for the hands.

Its cosmetic appeal merely adds an additional element to the user's pleasure.

We claim:

1. A water-in-oil emulsion containing an aqueous phase dispersed in an oily phase using an emulsifying agent, wherein the emulsifying agent is formed essentially of a mixed ester of isostearic acid and succinic acid with glycerol and wherein the aqueous phase of the emulsion additionally contains at least 10% by weight of polyol relative to the total weight of the emulsion.

2. An emulsion according to claim 1, wherein the oily phase contains volatile silicones.

3. An emulsion according to claim 1 or 2, wherein the oily phase represents from 10% to 45% by weight relative to the total weight of the emulsion.

4. An emulsion according to claim 2 or 3, wherein the oily phase contains at least one non-silicone-containing oil representing from 1% to 10% by weight relative to the total weight of the oily phase.

5. An emulsion according to claim 1, wherein the polyol represents up to 40% by weight relative to the total weight of the emulsion.

6. An emulsion according to claim 1, wherein the polyol represents from 10% to 20% by weight relative to the total weight of the emulsion.

7. An emulsion according to claim 1, wherein the polyol is at least one compound chosen from glycerol, mannitol and sorbitol.

8. An emulsion according to claim 1, wherein the polyol is glycerol.

9. An emulsion according to claim 1, wherein the mixed ester represents from 0.5% to 8% by weight relative to the total weight of the emulsion.

10. An emulsion according to claim 1, wherein the mixed ester represents from 2% to 6% by weight relative to the total weight of the emulsion.

11. An emulsion according to claim 1, wherein it additionally contains at least one adjuvant chosen from perfumes, hydrophilic active agents and lipophilic active agents, gelling agents for the aqueous and oil phases, dyestuffs, and preserving agents.

12. An emulsion according to claim 11, wherein the adjuvant represents from up to 5% by weight relative to the total weight of the emulsion.

13. A cosmetic composition, in the form of an emulsion according to claim 1.

14. A method for cosmetic treatment of the hands which comprises applying the emulsion of claim 13 to the hands.

15. A method for preparation of a cream intended for the dermatological treatment of the hands which comprises preparing the emulsion of claim 1 in the form of a cream.

* * * * *